(12) United States Patent
LaRose et al.

(10) Patent No.: US 8,961,390 B2
(45) Date of Patent: Feb. 24, 2015

(54) SENSORLESS FLOW ESTIMATION FOR IMPLANTED VENTRICLE ASSIST DEVICE

(71) Applicants: Jeffrey LaRose, Parkland, FL (US); Udai Singh, Cary, NC (US)

(72) Inventors: Jeffrey LaRose, Parkland, FL (US); Udai Singh, Cary, NC (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 13/939,964

(22) Filed: Jul. 11, 2013

(65) Prior Publication Data

US 2013/0296634 A1 Nov. 7, 2013

Related U.S. Application Data

(63) Continuation of application No. 13/027,811, filed on Feb. 15, 2011, now Pat. No. 8,506,470, which is a continuation of application No. 11/597,230, filed as application No. PCT/US2005/018333 on May 24, 2005, now Pat. No. 7,887,479, and a continuation-in-part of application No. 10/853,302, filed on May 25, 2004, now Pat. No. 7,591,777, said application No. 11/597,230 is a continuation-in-part of application No. 10/853,302, filed on May 25, 2004, now Pat. No. 7,591,777.

(51) Int. Cl.
*A61M 1/10* (2006.01)
*A61M 1/12* (2006.01)

(52) U.S. Cl.
CPC ............... *A61M 1/101* (2013.01); *A61M 1/122* (2013.01); *A61M 2205/3379* (2013.01)
USPC ............... 600/17; 600/16; 623/3.1; 623/3.13; 623/3.14; 623/3.15; 623/3.24; 623/3.25; 623/3.28

(58) Field of Classification Search
USPC ............ 623/3.1, 3.13, 3.14, 3.15, 3.24, 3.25, 623/3.28; 600/16, 17; 73/54.28, 54.38
See application file for complete search history.

(56) References Cited

U.S. PATENT DOCUMENTS

| | | | |
|---|---|---|---|
| 4,781,525 A | 11/1988 | Hubbard et al. | |
| 5,078,741 A | 1/1992 | Bramm et al. | |
| 5,725,357 A | 3/1998 | Nakazeki et al. | |
| 5,798,454 A | 8/1998 | Nakazeki et al. | |

(Continued)

FOREIGN PATENT DOCUMENTS

EP 1331017 A2 7/2003

OTHER PUBLICATIONS

Docter, A., Lösch, H., Wagner, W. A New Apparatus for Combined easurements of the Viscosity and Density of Fluids for Temperatures from 233 to 523 K at Pressures up to 30 MPa. International Journal of Thermophysics 20(2), 1999: 485-505.

(Continued)

*Primary Examiner* — Deborah Malamud
(74) *Attorney, Agent, or Firm* — Lerner, David, Littenberg, Krumholz & Mentlik, LLP

(57) ABSTRACT

A method of estimating the blood flow rate of a heart ventricle assist device which is positioned externally of, or implanted in, a patient. The assist device comprises a blood pump having a rapidly rotating, electrically powered impeller, and comprises briefly interrupting power to the impeller to cause its rotation to slow. From this, blood viscosity can be estimated, which viscosity is used to obtain real time, estimated blood flow rates and pressure heads. Apparatus for accomplishing this is disclosed.

21 Claims, 6 Drawing Sheets

(56) References Cited

U.S. PATENT DOCUMENTS

| | | | |
|---|---|---|---|
| 6,066,086 A | 5/2000 | Antaki et al. | |
| 6,135,943 A | 10/2000 | Yu et al. | |
| 6,149,683 A | 11/2000 | Lancisi et al. | |
| 6,158,984 A | 12/2000 | Cao et al. | |
| 6,234,772 B1 | 5/2001 | Wampler et al. | |
| 6,264,601 B1 | 7/2001 | Jassawalla et al. | |
| 6,368,083 B1 | 4/2002 | Wampler | |
| 6,447,441 B1 * | 9/2002 | Yu et al. | 600/16 |
| 6,540,658 B1 | 4/2003 | Fasciano et al. | |
| 6,623,420 B2 | 9/2003 | Reich et al. | |
| 6,634,224 B1 | 10/2003 | Schob et al. | |
| 6,640,617 B2 | 11/2003 | Schob et al. | |
| 6,711,943 B1 | 3/2004 | Schob et al. | |
| 6,817,836 B2 | 11/2004 | Nose et al. | |
| 6,866,625 B1 | 3/2005 | Ayre et al. | |
| 6,889,082 B2 | 5/2005 | Bolling et al. | |
| 6,949,066 B2 | 9/2005 | Bearnson et al. | |
| 2005/0267322 A1 | 12/2005 | LaRose et al. | |
| 2007/0232934 A1 | 10/2007 | LaRose et al. | |

OTHER PUBLICATIONS

Evers, C., Lösch, H.W., Wagner, W. An Absolute Viscometer-Densimeter and Measurements of the Viscosity of Nitrogen, Methane, Helium, Neon, Argon and Krypton over a Wide Range of Density and Temperature. International Journal of Thermophysics 23(6), 2002: 1411-1439.

International Preliminary Report on Patentability issued by the International Bureau of WIPO on Nov. 29, 2006 in connection with International Application No. PCT/US2005/0183333.

Office Action issued Sep. 30, 2009 in connection with U.S. Appl. No. 11/597,230, filed Dec. 27, 2006.

Office Action issued Jan. 27, 2010 in connection with U.S. Appl. No. 11/597,230, filed Dec. 27, 2006.

Office Action issued Apr. 27, 2010 in connection with U.S. Appl. No. 11/597,230, filed Dec. 27, 2006.

Notice of Allowance issued Nov. 26, 2010 in connection with U.S. Appl. No. 11/597,230, filed Dec. 27, 2006.

Supplementary European Search Report issued by the European Patent office on Jan. 9, 2012 in connection with European Patent Application No. 05755086.5.

PCT International Search Report issued by the International Searching Authority on Apr. 19, 2006 in connection with PCT/US2005/01833.

Written Opinion of the International Searching Authority issued by the International Searching Authority in connection with PCT/US2005/01833.

Office Action issued Oct. 16, 2012 in connection with U.S. Appl. No. 13/027,811, filed Feb. 15, 2011.

Amendment in Response to Oct. 16, 2012 Office Action, filed Feb. 19, 2013, in connection with U.S. Appl. No. 13/027,811, filed Feb. 15, 2011.

Notice of Allowance issued Apr. 3, 2013 in connection with U.S. Appl. No. 13/027,811, filed Feb. 15, 2011.

\* cited by examiner

HEARTWARE VAD PERFORMANCE PUMP FLOW VERSUS PUMP HEAD FOR VARIOUS RPM'S

INFLUENCE OF VISCOSITY ON PUMP PERFORMANCE 3000 RPM

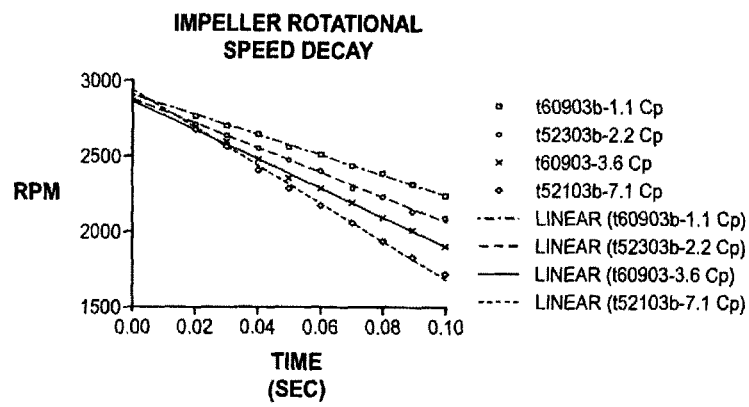
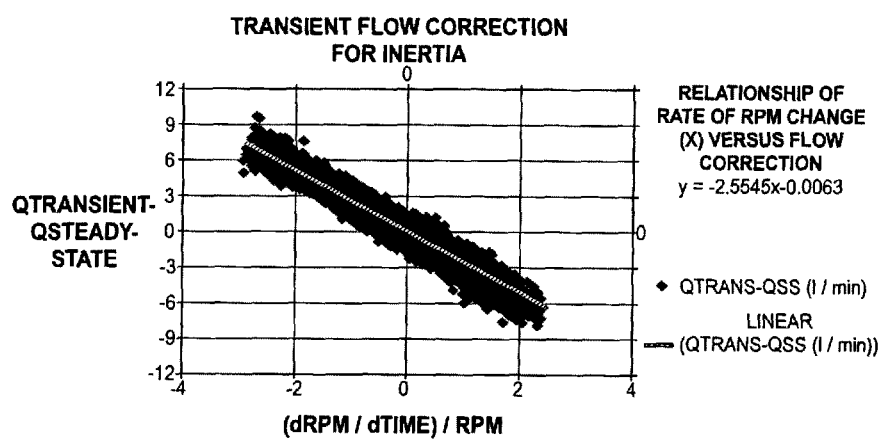

SENSORLESS FLOW ESTIMATION FOR IMPLANTED VENTRICLE ASSIST DEVICE

This application is a continuation of U.S. application Ser. No. 13/027,811, filed Feb. 15, 2011, now U.S. Pat. No. 8,506,470, which is a continuation of U.S. application Ser. No. 11/597,230, filed Dec. 27, 2006, now U.S. Pat. No. 7,887,479, issued Feb. 15, 2011, which is a §371 national stage of PCT International Application No. PCT/US2005/018333, filed May 24, 2005, and a continuation-in-part of U.S. application Ser. No. 10/853,302, filed May 25, 2004, now U.S. Pat. No. 7,591,777, issued Sep. 22, 2009, the contents of which are hereby incorporated by reference into this application.

BACKGROUND OF THE INVENTION

The measurement of blood flow is an essential component for physiological control of a ventricle assist device, to assist the heart in functioning. Such devices are well known, and, as indicated for example in U.S. Pat. Nos. 6,149,683; 6,158,984; 6,234,772; and 6,368,083 may comprise a blood pump having a rapidly rotating, electrically powered impeller for pumping of blood, generally in a supplemental manner, to assist a failing heart. However, too much flow through the ventricle assist device (VAD) can lead to ventricle collapse and damage to the myocardium. Too little flow can result in the VAD not producing proper therapeutic support for the patient. Thus, the blood flow provided by the VAD must be closely monitored at all times.

For a VAD utilizing a rotary pump, the only parameters which are available for flow estimation, in the absence of supplemental sensors, are the rotational speed of the impeller and the power or the electrical current passing through the electric motor. Such sensorless flow estimation can be determined through sensing of the current or the back EMF of the system.

Rotary pumps of the type described above have a characteristic performance curve, such as the pressure head-flow curve, which relates the pump head and the blood flow rate provided by the pump at a given rotational speed for the impeller. "Pump head" is related to the pressure increase created by the pump, and is a known term. Such a standard curve is used to help select the appropriate pump for a given system application. However, a problem arises in the obtaining of a reliable flow estimate for a particular clinical situation, using the standard performance curves for a particular pump. This arises from the fact that the viscosity of a patient's blood is variable to an extent, a sufficient extent to render estimated pump flow rates inaccurate unless the current blood viscosity is known. The patient's health, gender, degree of hydration, hematocrit and certain medications can affect blood viscosity to a degree that is sufficient to throw off estimates of pump flow based upon the pump power and/or rotational speed. Thus, a periodic measurement of blood viscosity is needed in order to maintain the accuracy of VAD flow and pressure head estimation.

Thus, without careful and continuous monitoring of the viscosity of the blood of the patient, one cannot obtain an accurate estimate of the flow rate of the blood pumped by the VAD. This, of course, renders difficult or impossible an estimate on how the native heart is performing, and other clinical data becomes effectively unavailable from the data that can be obtained from the ventricle assist pump device itself. Thus, it becomes necessary to utilize differential pressure sensors and the like to obtain better data. Without such sensors, much accurate clinical data pertaining to the patient has been unavailable from an analysis of data from the VAD pump.

DESCRIPTION OF THE INVENTION

In accordance with this invention, an external or internally implanted ventricle assist device is provided, typically having a pump impeller suspension system that uses hydrodynamic thrust bearings for axial constraint. Examples of these are as described in the patents cited above.

Specifically, this invention relates to a heart ventricle assist device. The device comprising a blood pump having a rapidly rotating, electrically powered impeller; means for briefly interrupting power to the impeller to cause its rotation to slow; and means for determining the rate at which the rotation slows without applied power.

In some embodiments, the apparatus further includes means for measuring changes in impeller rotational speed over time periods of less than about 0.1 second each. Also, the means for applying power to the blood pump can optionally be varied in a manner that is a function of the changes in impeller rotational speed, which means for measuring changes in impeller rotational speed may preferably use a current sensing technique or a back EMF force signal. By this invention, blood flow sensors and pressure sensors may optionally not be used.

The invention of this application also comprises a method of monitoring a heart ventricle assist device which is connected to a patient, the assist device comprising a blood pump having a rapidly rotating, electrically powered impeller. The method comprises: briefly interrupting power to the impeller to cause its rotation to slow; and estimating the blood viscosity of the patient from the rate at which the rotation slows without applied power.

Thrust bearings naturally encounter a drag as they rotate. Further by this invention, the viscosity of the blood may be predicted for a VAD, by depowering the impeller and monitoring the rotational speed decay rate, which is generally proportional to viscosity of the blood. Thus, the viscosity of the blood can be quickly and easily estimated by measurement of the rotational speed decay rate of the impeller, typically for a time period which is no more than about 100 milliseconds, after which time the power is reapplied again. Thus, the patient does not suffer a severe, deleterious effect from the process.

In this period of no more than about 100 milliseconds, a current design of ventricle assist device of HeartWare, Inc. has a drop in rotational speed of about 750-1250 rpm from a 3000 rpm initial speed in a period of less than 100 milliseconds, this data being relatively independent of the pressure head loading on the impeller, and, therefore does not require synchronization with the native heart of the patient in which the ventricle assist device is implanted.

Furthermore, one may estimate a steady state blood flow rate, calculated from (1) the estimated blood viscosity as acquired above, (2) the present magnitude of the power applied to the VAD, and (3) the present rotational speed of the impeller.

These data provide the physician with information on the functioning of the blood pump, to assist in the control of the pumped flow rate, to maximize benefit to the patient.

The ventricle assist device may be externally or internally implanted, and controlled in response to knowledge of the estimated, steady state blood flow rate and/or in response to other data that may be available, such as the blood oxygen saturation level and the like. The pump rotational speed may be raised or lowered as may be appropriate for optimal pumping rates under the conditions of the moment. The rotational speed of the blood pump may be varied for conventional reasons as dictated by oxygen saturation or the like, but the pump rotational speed and power applied may also be varied in a manner that is a function of the estimated blood viscosity, typically after utilizing that data to obtain an estimated steady state blood flow rate. The rotational speed then may be varied as conditions change, to maintain a desired, steady state flow rate.

An additional difficulty in estimating flow rate within a patient is that the body system resistance varies with time. A body's physiologic needs varies with activity and level of stress or anxiety. A rotary ventricular assist device may have to change rotational speed to best meet the transient, physiological needs. The steady state, conventional head-flow curves do not take into account the impeller inertia, or the lag time to change rotary speeds. An empirical relationship can be developed between the rate of change of rotational speed and the difference of actual flow rate and steady-state flow rate. This correction term can allow the estimation of instantaneous flow rates, which may vary over a very short period of time ranging down to about 10 milliseconds. An analogous relationship can be developed for pump head pressures.

In accordance with this invention, in a series of time periods typically of less than 0.1 second each, transient changes in impeller rotational speed may thus be measured, and an estimated flow deviation from the estimated, steady state blood flow rate may be calculated, to provide an estimated, transient flow rate for each of the time periods. These transient changes may be expressed as an impeller inertia correction term which relates (1) the time rate of change of the rotational speed of the impeller and (2) the difference between the transient flow rate and the steady state flow rate.

By the use of this transient blood flow rate, and/or the impeller inertia correction term for such brief time periods, one can vary the rotational speed applied to the blood pump in a manner that is a function of the estimated, transient blood flow rate for each time period.

The result of this is to provide a surprising accuracy to the estimated VAD blood flow rate (and pump head) to recognize the transient changes of impeller rotation over time. These transient changes can be charted with the time periods mentioned above being down to about the 10 millisecond level, to create a chart of pump head variation over time and pump flow over time. From these curves the actual beating of the natural heart can be recognized, and, in the manner of a cardiogram, it is believed that functioning of the valves and most or all of the data that can be achieved from a cardiogram can be observed in accordance with this invention, merely from the raw data of the pump impeller rotation rate and the power (or absence thereof) applied to the pump. These data may be electronically monitored by the VAD, so that the pumping rate of the VAD may be optimally controlled, and data from the native heart may be determined throughout the days and nights without the need of setting up a cardiogram for the patient. Thus, the condition of the native heart may be more easily monitored over the passage of time by the cardiologist. Particularly, the native heart flow rate and other real time diagnostic information may be provided for the attending physician, while the flow and pump head estimates can be used to determine cardiovascular resistance characteristics.

DESCRIPTION OF THE DRAWINGS

FIG. 3 is a graph showing the rate of decay of impeller rotational speed for the same HeartWare VAD pump used, over time from shutoff of power. The different curves show differing blood viscosities, and illustrate the strong effect of blood viscosity.

FIG. 4. shows the influence of the same VAD impeller and motor inertia as it effects blood flow changes, compared with rotation speed changes.

DESCRIPTION OF SPECIFIC EMBODIMENTS

Figure 8:
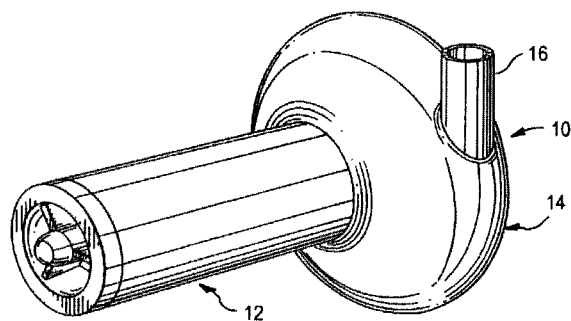
FIG. 8 is a front perspective view of an illustrative embodiment of the blood pump used in this present invention.

Referring to the drawings, (FIG. 8) rotary blood pump 10, which is of a specific type disclosed in Wampler et al. U.S. Pat. No. 6,234,772, the disclosures of which are incorporated by reference herein, includes a housing having an elongated inlet 12 and an impeller casing or volute 14. A discharge tube 16 extends through the housing to communicate with the interior of impeller casing 14.

Figure 9:
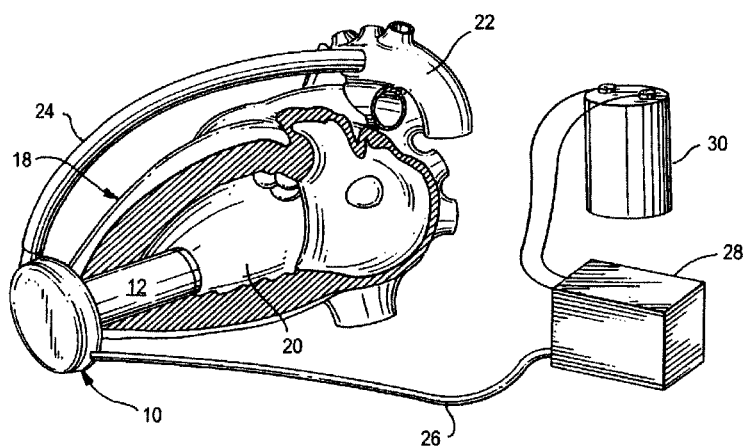
FIG. 9 is a simplified, fragmentary representation of a human heart, showing the blood pump of FIG. 1 implanted within the left ventricle of the heart.

An illustrative arrangement for the anatomical placement of pump 10 is shown in FIG. 9. A simplified representation of a heart 18 includes a left ventricle 20 and an aorta 22. Inlet tube 12 serves as an inflow cannula, and is placed into the apex of the left ventricle 20. An arterial vascular graft 24 is connected on one end to discharge tube 16 and on the other end to aorta 22 through an end-to-side anastomosis. Pump 10 is connected by means of insulated cable 26 to a controller 28 and a power supply 30. Controller 28 and power supply 30 may be worn externally, or, alternately, may be implanted. Rather than using wires, a transcutaneous controller and power transmission could be used.

Figure 10:
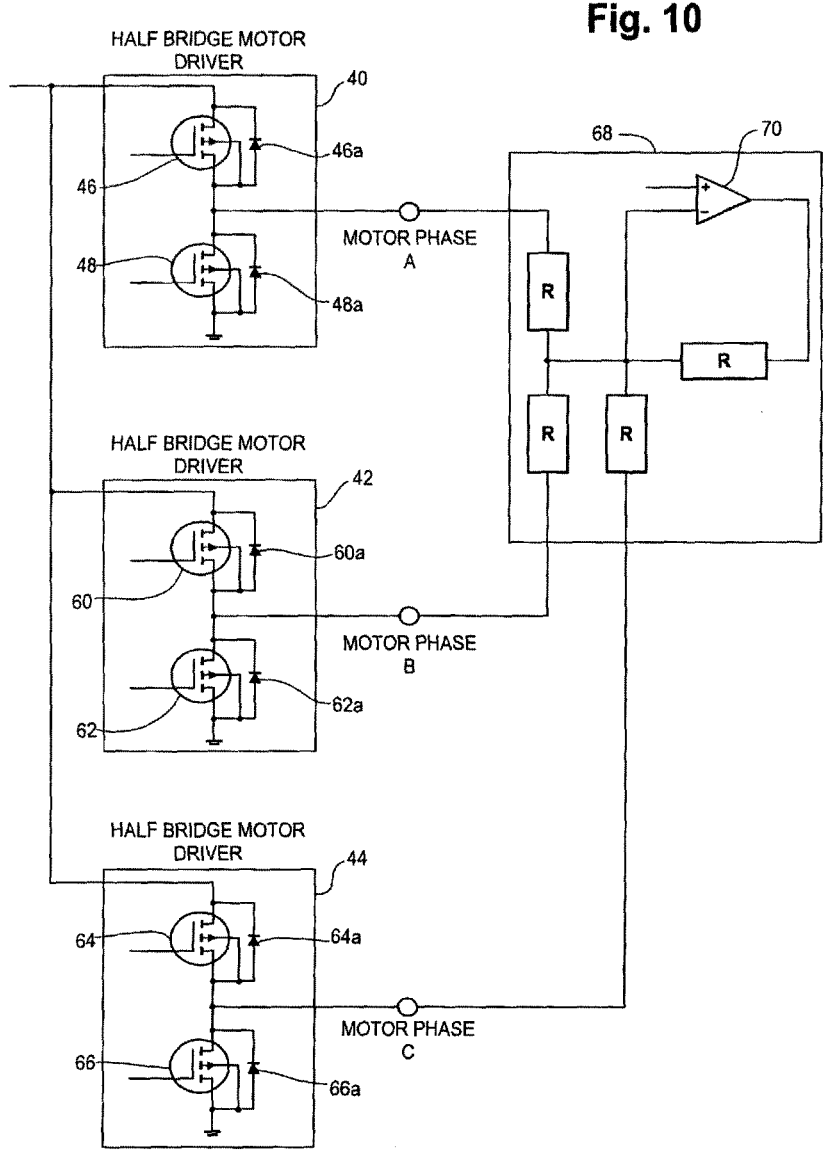
FIG. 10 is a flow chart showing how the pump of FIGS. 8-9 can be intermittently depowered and the decay rate (slowing) of its rotation determined, to permit estimation of the blood viscosity.

Along with other circuitry, appropriate circuitry to monitor the pump impeller rotation rate may be included in controller 28, such as that as suggested by FIG. 10; or other, appropriate circuitry of a type readily understood by those skilled in the art.

Three half bridge motor drivers 40, 42 and 44 are provided as illustrated in FIG. 10. The first motor driver 40 includes two r-channel MOSFETs 46 and 48 expectedly having body diodes 46*a* and 48*a* across each MOSFET's drain and source. The second half bridge motor driver 42 includes a pair of r-channel MOSFETs 60 and 62, expectedly having body diodes 60*a* and 62*a* across each MOSFET's drain and source. The third half bridge motor driver 44 includes a pair of r-channel MOSFETs 64 and 66, expectedly having body diodes 64a and 66a across each MOSFET's drain and source.

In order to free wheel the pump during coastdown without power, the motor voltage regulator has to continue switching in order to output a steady DC voltage that is greater than the positive peak of the back EMF signals from the motor. This is in order for the body diodes to not conduct and thereby actively brake the pump. One preferably keeps the regulator running at a DC level higher than the anticipated, peak to peak motor waveforms during coast down.

The pump's back EMF signals have also to be subsequently biased so they are similarly not clipped at levels below 0V (ground). This biasing can be accomplished using the very same circuitry that measures the zero crossings of the back EMF signals during active motor commutation. The three phases are input to a summing amplifier 68, which is used during normal operation of the VAD motor. A virtual reference voltage is provided through the inverting input of the op-amp 70 used in the summing amplifier. A high impedance Input that provides a reference such as that described is able to bias the neutral point of the three phase motor. The reference voltage is a function of the motor voltage regulator, which at the onset of coastdown can be set to a level that satisfies the conditions of preventing clipping both the positive and negative peaks of the back EMF signal.

The three phases are hence individually tracked and measured with ease by directly sampling signals through resistive division. The coastdown decay constant can be directly determined from the values and time between minimum and maximum points of the back EMF signals. The signals are also continuously monitored to track the position of the pump impeller so that re-establishing motor control is accomplished seamlessly by re-engaging the motor drive waveforms with an appropriate frequency and amplitude.

The specific ventricle assist device that was experimentally used in the work reported herein was a HeartWare ventricle assist device, although it is believed that other systems with VADs having a rotating impeller may be used as well. The invention may be practiced with a VAD which has been implanted into a patient, to assist the heart in providing adequate blood flow to the body, though the invention is not limited to just this application.

In the specific embodiment of the invention as disclosed herein, the blood viscosity is estimated by depowering the impeller as previously described, this being done at prescribed intervals of several times per day, since blood viscosity can change fairly quickly.

By this invention, (a) the implanted VAD rotational speed may be brought to a designated level, for example, 3,000 rpm.

(b) The motor commutation (motor power) may be suspended for an interval typically on the order of 20 to 100 milliseconds. This period of time is short enough to (1) limit the impeller rotational speed drop to a range that is typically on the order of about 750 to 1250 rpm, so that the impeller does not stop spinning. Thus, there is no interference with the necessary provision of therapeutic support, and the measurement accuracy is also facilitated.

(c) The rotational speed decay is monitored through either current sensing techniques or through the back EMF force signals. The previously described technique of FIG. 10 may be used.

(d) This measured rotational speed decay rate may be compared to an empirically determined relationship: basically a chart, electronic or otherwise, in which the speed decay rate for the particular pump and rotation speed, and the blood viscosity, are related by a curve which has been previously determined at selected, time intervals with no power applied. See FIG. 3.

(e) Then, motor commutation (power) is re-established so that the pump continues its function with only a fraction of a second hiatus.

(f) Following this, the steady-state blood flow rate through the ventricle assist device (and also the pump head if desired) may be determined.

Figure 7:
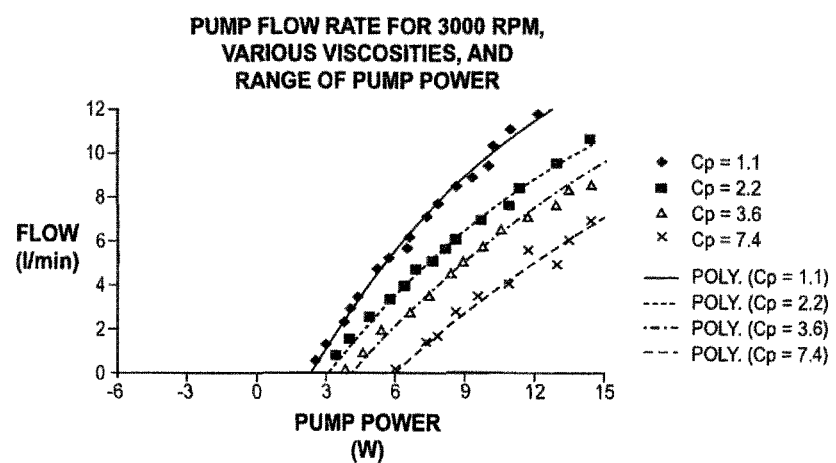
FIG. 7 is a graph comparing pump flow rate at various blood viscosities and pump power.

Such steady state performance curves may be empirically obtained through bench testing. See for example FIG. 7, where the steady state pump flow rate may be estimated from the power applied to the pump through knowledge of the blood viscosity. Various empirical graphs may be provided, and electronically stored in the system, providing data at various impeller rotation rates or other variables. FIG. 7 is for a rotation rate of 3,000 rpm.

Thus, the steady state VAD flow rate is calculated, using the just-determined blood viscosity, the present motor power (or current), and the particular impeller rotational speed. This steady state flow rate is a critical piece of clinical data, and may be compared with predetermined flow rate limits and the like to confirm that the VAD is providing a proper flow rate for the circumstance. Thus, one can assure, for example, that the flow rate does not fall out of a predetermined, desired clinical range, thus maximizing clinical benefit to the patient. Also, functioning of the pump may be monitored in this manner.

However, further by this invention, the data generated from the impeller rotation rate and the power applied to the pump may be obtained and processed in a manner which may provide critical, added information concerning not only the pump operation but the condition of the native heart itself, and other clinical aspects of the patient's progress or maintenance. These data may be used to monitor transient VAD behavior, to improve the accuracy of the steady state data which is provided to estimate VAD performance.

More specifically, over a series of time periods, each of which is typically less than 0.1 second, transient changes in the impeller rotational speed may be measured. For each of these impeller speeds as measured, for a particular power or current applied, an estimated flow deviation from the estimated, steady state blood flow rate may be calculated, to provide an estimated, transient flow rate for each time period. These transient changes may be expressed as an impeller inertia correction term, which relates the time rate of change of rotational speed to the difference between the transient flow rate and the steady state flow rate.

To accomplish this, inertia correction factors for the VAD flow rate (and the pressure head if desired) can be generated through bench testing to provide empirical graphs or charts. These data should encompass the possible range of heart beat rates, transient rotational speed changes, and cardiovascular resistance, to provide an empirical database as shown in FIG. 4. That graph correlates for particular conditions the error from the steady state blood flow rate for a given, short (preferably 10-100 milliseconds) time period as a function of changes in the impeller rotation speed. The specific error value can then be applied to the steady state flow rate to provide an estimated, transient flow rate for each time period.

This, in turn, may be part of a feedback loop in which the power applied to the blood pump may be varied in a manner that is a function of the estimated, transient blood flow rate for each time period.

Figure 1:
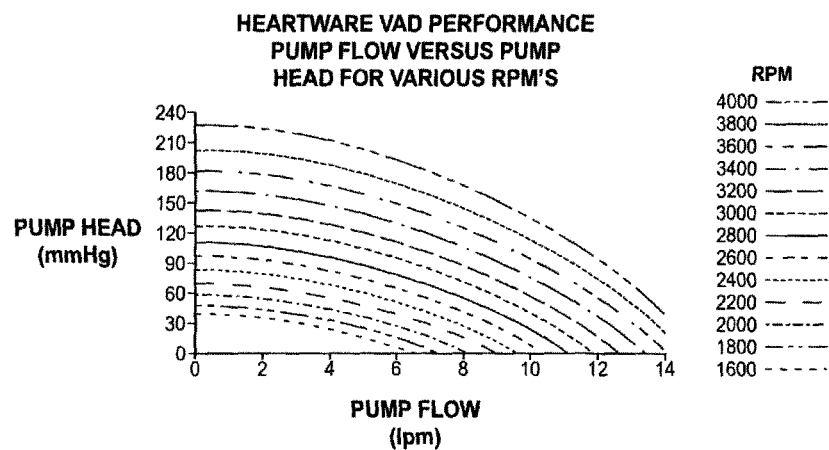
FIG. 1 is a graph showing the relationship of pump head in mm. Hg to pump flow rates in liters per minute for a VAD blood pump of HeartWare, Inc. The various curves represent the data for various pump rotation speeds in rpm.
Figure 2:
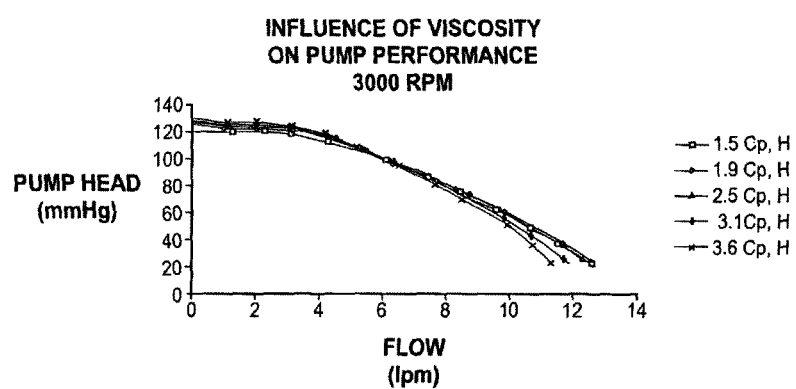
FIG. 2 is a graph showing the influence of viscosity of the blood on pump flow rates at varying powers applied to the same HeartWare pump, where the impeller is rotating at 3,000 rpm. The various curves represent varying blood viscosities expressed in centipoises at 37° C.
Figure 5:
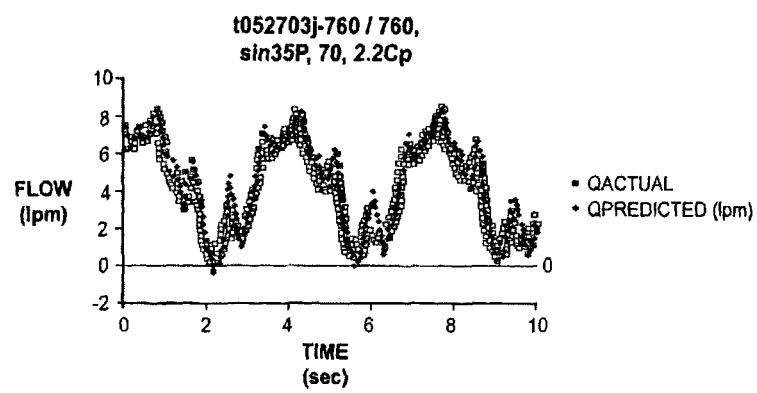
FIG. 5 is a graph of transient flow rates, comparing the flow predicted using the disclosed method ("Q predicted") and the values from an ultrasonic flow probe ("Qactual").

Results comparing measured and estimated VAD flow rates (and pump heads) under conditions of varying rotational speed (rpm) ramp and varying system resistance for a prescribed heart rate using the above-described procedure are shown in FIG. 5, which relates the flow through the blood pump over a brief period of time in a series of about 20-30 millisecond time periods. A series of large oscillations are seen, which come from an intentionally programmed, cyclic variation of power to the pump. The smaller peaks reflect the individual heart beats of the native heart, showing that, if desired, with removal of the large, planned oscillations caused by varying power applied to the pump, a constant power graph which is rather similar to a cardiogram can be achieved, in which heart function can be monitored in a manner similar to that of a cardiogram, except that the data shown is obtained from transient variations in impeller rotational speed, measured over time periods that typically represent a few milliseconds each.

Thus, not only can the ventricle assist device be monitored in its functioning, but additional benefits of accurate, transient flow rates can be converted into estimates of native heart flow rate and real time diagnostic information for the attending physician.

In a similar manner, a steady state blood pressure head may be estimated from the estimated blood viscosity, the present magnitude of the power applied, and the present rotational speed of the impeller for added clinical data as may be desired. Also, the transient changes in the impeller rotational speed may be used to estimate transient pressure head changes, for similar clinical benefit.

EXAMPLE

An in vitro test of blood pumping was performed, using a Heartware VAD.

Step 1. Obtain Fluid Viscosity

The rotational speed decay was monitored by depowering the impeller of the VAD while it was initially operating at 3,000 rpm. The rotational speed decay was measured in accordance with the Table I below:

We collected rotational speed (i.e., RPM) for several time increments to obtain the rotational speed decay rate after depowering:

TABLE I

| Time (sec) | RPM |
| --- | --- |
| 0.00 | 3000 |
| 0.02 | 2840 |
| 0.04 | 2680 |
| 0.06 | 2515 |

Using a linear curve fitting routine, the initial rotational speed decay rate (i.e., dRPM/dTime is determined to be −8080 RPM/sec from the Table 1 data. An empirical relationship that characterizes the rate of rotational speed decay rate vs. fluid viscosity can be developed prior to installation of a VAD in a patient. Such a relationship is illustrated in FIG. 6, and is determined for the particular pump by experimentation.

The calculated speed decay rate (−8080 RPM/sec.) may then be used to obtain a computed viscosity as illustrated below.

Viscosity=−0.001007*(−8080 RPM/sec)−5.908*=2.2 Centipoises (Cp).     A.

Figure 6:
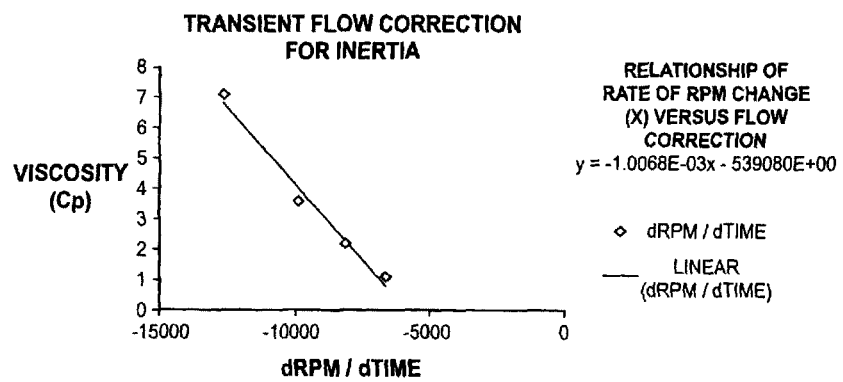
FIG. 6 is a graph of blood viscosity vs. dPump RPM/dTime.

The starred terms represent the shape of the empirically determined curve of FIG. 6.

Step 2. Re-establish Motor Commutation
Step 3. Obtain Motor Parameters to Estimate Flow Rate
The data of Table 2 was collected from the running motor.

TABLE 2

| Motor Parameters | |
| --- | --- |
| Power | 12.13 Watts |
| RPM | 3006 |
| dRPM/dTime | 0.80 |

Step 4. Calculating of the Steady-State Flow Rate.

The Steady-State Flow Rate is calculated from the appropriate empirical relationship from FIG. 7 for a given RPM, and the calculated blood viscosity of 2.2 Cp.

An empirical relationship that characterizes the pump flow rate for a given rotational speed, fluid viscosity, and pump power can be determined prior to the experiment for the VAD used. An example of such an empirical relationship is shown at FIG. 7 for the steady state pump flow rate of 3,000 RPM, at varying viscosities. This empirical relationship may be expressed as B. Pump flow rate (Qss=−4.112*+1.406*(12.13 Watts–from Table 2)−0.026*(12.13 Watts)$^2$=9.12 l/min.     B.

The starred terms reflect the shape of the empirically determined curve for flow vs pump power. The curve with horizontally square points is the one used here, for a viscosity 2.2 Cp.

Step 5. Adjust the Flow Rate Estimate for Transient Inertia using another Empirical Relationship for a Given Rate of Rotational Speed Change.

The relationship between the difference in actual flow rate and steady state flow rate, (which in this embodiment was previously calculated to be 9.12 l/min), can be characterized as a function of the rate of rotational speed change. FIG. 4 is an example of the development of such a relationship, the data being empirically determined for the particular pump.

This can be expressed as follows:

Qestimate=Qss−2.5545*(dRPM/dTime/RPM)−0.0063*     C.

The starred terms are once again describing the empirically obtained data curve, in this case from FIG. 4. Solving equation C we have:

Qestimate=9.12 l/min−2.5545*(0.80)−0.0063=7.11/min     D.

Note that for this particular test of this example, the measured flow rate was 6.5 l/min. Thus, the overall error was 9%, which is considered by the targeted industry to be very good. Without such corrections, the error can be 40%.

The above has been offered for illustrative purposes only, and is not intended to limit the scope of this invention, which is as defined in the claims below.

That which is claimed is:

1. A method of measuring a rate of change in the rotational speed of a rotating impeller within a blood pump and determining blood viscosity comprising the steps of:
    applying electrical power to rotate the impeller;
    monitoring the rotational speed of the impeller;
    monitoring back EMF signals created by the rotational speed of the impeller;
    determining a transient rate of change in rotational speed of the impeller from at least the back EMF signals created by a change of rotational speed of the impeller during a predetermined time period; and
    using the transient rate of change in rotational speed of the impeller to determine the viscosity of the blood in the pump, wherein viscosity of the blood is determined when the pump is implanted in a subject.

2. The method of claim 1 comprising interrupting the applied electrical power for the predetermined time period to cause the rotational speed of the impeller to slow.

3. The method of claim 2 comprising interrupting the applied electrical power for less than about 0.1 seconds.

4. The method of claim 3 comprising interrupting the applied electrical power for no more than 100 milliseconds.

5. The method of claim 4 comprising interrupting the applied electrical power for between 20 and 100 milliseconds.

6. The method of claim 4 comprising interrupting the applied electrical power for between 10 and 100 milliseconds.

7. The method of claim 2 comprising determining from the back EMF signals a rotational speed decay rate of the impeller.

8. The method of claim 7 comprising determining the rotational speed decay rate from the values and time between minimum and maximum points of the back EMF signals.

9. The method of claim 7 in which blood flow sensors and pressure sensors are not used.

10. A method of measuring a rate of change in the rotational speed of a rotating impeller within a blood pump and determining blood viscosity comprising the steps of:
    applying electrical power to rotate the impeller;
    monitoring the rotational speed of the impeller;
    determining a transient rate of change in rotational speed of the impeller during a predetermined time period; and
    using the transient rate of change to determine the viscosity of the blood in the pump,
    wherein viscosity of the blood is determined when the pump is implanted in a subject.

11. The method of claim 10 comprising interrupting the applied electrical power for a predetermined time period to cause the rotational speed of the impeller to slow.

12. The method of claim 11 comprising interrupting the applied electrical power for less than about 0.1 seconds.

13. The method of claim 12 comprising interrupting the applied electrical power for no more than 100 milliseconds.

14. The method of claim 13 comprising interrupting the applied electrical power for between 20 and 100 milliseconds.

15. The method of claim 13 comprising interrupting the applied electrical power for between 10 and 100 milliseconds.

16. The method of claim 10 wherein either the back EMF signals or a current sensing technique is used to determine the transient rate of change of rotational speed of the impeller.

17. The method of claim 16 further comprising determining a rotational speed decay rate of the impeller.

18. The method of claim 17 comprising determining the rotational speed decay rate from the values and time between minimum and maximum points of the back EMF signals.

19. The method of claim 17 in which blood flow sensors and pressure sensors are not used.

20. A method of measuring a rate of change in the rotational speed of a rotating impeller within a blood pump and determining blood viscosity comprising the steps of:
    applying electrical power to rotate the impeller;
    monitoring the rotational speed of the impeller;
    determining a transient rate of change in rotational speed of the impeller during a portion of a predetermined maximum time period utilizing a current sensing technique; and
    using the transient rate of change to determine the viscosity of the blood in the pump,
    wherein viscosity of the blood is determined when the pump is implanted in a subject without the use of blood flow sensors or pressure sensors.

21. The method of claim 20 in which the pump is in vivo.

* * * * *